US00PP10636P

United States Patent [19]

Engelke

[11] Patent Number: Plant 10,636

[45] Date of Patent: Oct. 6, 1998

[54] 'DIAMOND' ZOYSIAGRASS PLANT

[75] Inventor: Milton Charles Engelke, Parker, Tex.

[73] Assignee: The Texas A&M University System, College Station, Tex.

[21] Appl. No.: 851,979

[22] Filed: May 6, 1997

[51] Int. Cl.[6] ..... A01H 5/00

[52] U.S. Cl. ..... Plt./90

[58] Field of Search ..... Plt./90

*Primary Examiner*—James R. Feyrer
*Assistant Examiner*—Kent L. Bell
*Attorney, Agent, or Firm*—Fulbright & Jaworski L.L.P.

[57] ABSTRACT

An asexually reproduced variety of perennial zoysiagrass with a unique combination of characters including an absence of leaf blade hairs, deep rhizomes, good recovery from sod harvest, high salinity tolerance, good shade tolerance, and a distinct DNA fingerprint.

2 Drawing Sheets

BACKGROUND OF THE INVENTION

Field of Invention

The present invention relates to a new and distinct asexually reproduced variety of perennial zoysiagrass (*Zoysia marrella* (L.)) Merr.

BRIEF SUMMARY OF THE INVENTION

This invention relates to a new and distinct perennial zoysiagrass cultivar identified as 'Diamond' zoysiagrass (herein after referred to as 'Diamond'), which was tested as 'DALZ8502'. 'Diamond' was discovered and identified at Dallas, Tex., as an aberrant selection in cultivated turf plots that were previously planted to a series of zoysiagrass plant introduction and commercial cultivars, including 'Meyer' and 'Emerald'. It was identified as a superior turf compared to other zoysiagrasses in its recuperative ability after sod harvest, its shade tolerance and salinity tolerance. 'Diamond' is an aggressively spreading *Zoysia matrella* (L.) Merr. that is appropriate for use in full sun to shaded tee boxes and greens in the coastal states, wherever zoysiagrass is adapted.

For purposes of registration under the "International Convention for the Protection of New Varieties of Plants" (generally known by its French acronym as the UPOV Convention) and noting Section 1612 of the Manual of Plant Examining Procedure, it is proposed that the new variety of zoysiagrass of the present invention be named 'Diamond' Zoysiagrass.

BRIEF DESCRIPTIONS OF THE ILLUSTRATIONS

FIG. 1 is a photograph of the leaf blade and of the inflorescence of 'Diamond'.

DETAILED DESCRIPTION OF THE INVENTION

Figure 2:
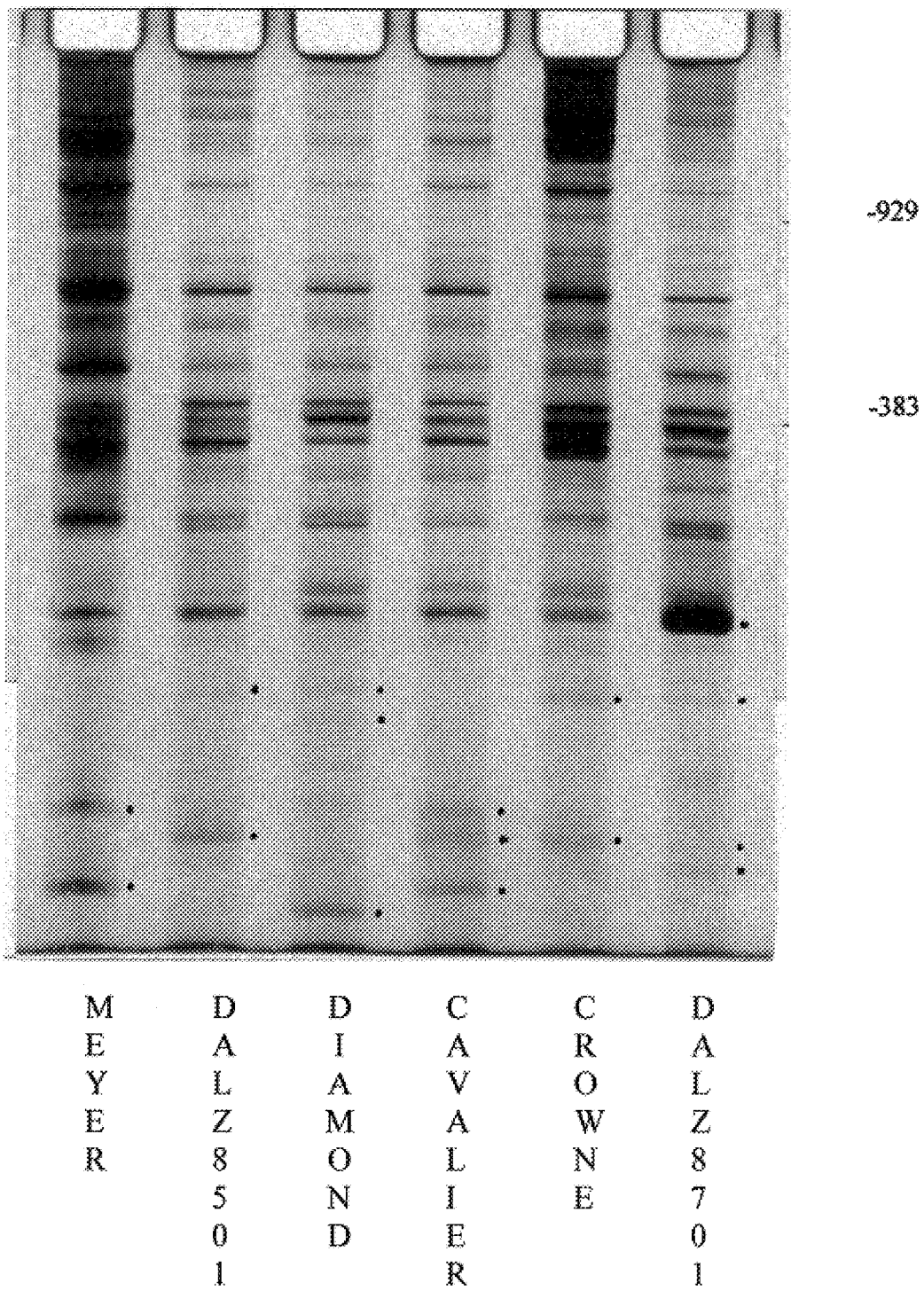
FIG. 2 is a DNA fingerprint of 'Diamond' in contrast to 'Meyer' zoysiagrass.

'Diamond' was characterized in greenhouse and field conditions. 'Diamond' is a unique variety of zoysiagrass (*Zoysia matrella* (L.)) Merr. that was discovered under cultivated conditions described above. 'Diamond' was vegetatively propagated and reproduced. 'Diamond' has been propagated by sod, plugs, springs, and stolons. Seed reproduction with self-fertility is not common in the Zoysia sp.

No seedling establishment from 'Diamond' has been noticed in either greenhouse or field studies.

'Diamond' is distinguished from other varieties of zoysiagrass by the combination of characters of shade tolerance, salinity tolerance, and turf quality. 'Diamond' is closest in appearance to the variety 'Emerald' zoysiagrass. 'Diamond' generally lacks winter hardiness such that it is recommended for use south of Red River (Texas-Oklahoma) and in the coastal plain states.

'Diamond' reproduces by rhizomes and stolons. 'Diamond' produces rhizomes that grow to a depth of 4–6", depending on maintenance programs. The stolons of 'Diamond' have a mean internode length of 6.4 mm between the fourth to the fifth node, 15.5 mm between the second and third nodes, with a mean stolon width and diameter from 0.79 to 0.88 mm (Tables 1, #2). These stolons and rhizomes root adventitiously at the nodes. Color notations of plant tissues were based on the Munsell *Color Charts for Plant Tissues,* Munsell Color, Baltimore, Md., 1977. Light quality, photoperiod, and general growth of the plants affect color notations. The internode color of 'Diamond' stolons exposed to full sun of is 5R 3/4.

Leaf blades of 'Diamond' are rolled in the bud, and are flat and stiff. The leaf blade length of 'Diamond' ranges from 22.7 to 42.0 mm and from 0.95 to 1.28 mm in width (Table 3, #4, #5), shorter and narrower than 'Emerald', 'El Toro', and 'Meyer'. There are not any hairs on the abaxial/adaxial leaf surfaces of 'Diamond'. Measured under greenhouse conditions in January 1996, the genetic, adaxial leaf color of 'Diamond' is 2.5 GY 5/2 to 2.5 G 5/2, with 'El Toro' having a leaf color of 2.5 GY 5/2, and 'Meyer' having a color of 2.5 G 3/4. The ligule of 'Diamond' is a row of silky hairs, approximately 2.1 to 2.6 mm in length on the longest hairs.

The flag leaf length of 'Diamond' is a mean of 3.69 cm when measured in a greenhouse, Dallas, Tex., January 1996. 'Diamond' has yellow-green anthers, fading to purple, colored anthers and white colored stigmas, undistinguished in shade of color. The inflorescence of 'Diamond' is a terminal spike-like raceme, with spikelets on short pedicels. 'Diamond' has a mean culm length of 2.40 cm, a floral region of 9.32 mm, with a mean of 10.3 florets per raceme.

The chromosome number of 'Diamond' is 40.

'Diamond' has tremendous sod harvest potential because of its strong rhizome system (Tables 6, #7). In trials at Dallas, Tex., established in 1983 and harvested in 1985 with a sod harvester, 'Diamond' showed high recovery in number of plants. 'Diamond' showed 22.5 and 93.8 plants per square foot at 19 and 42 days after harvest, respectively. 'Emerald' showed only 8.7 and 30.3 plants per square foot, with 'Meyer' having only 2.5 and 11 plants after 19 and 42 days, respectively. Compared to 'Meyer', 'Diamond' produced 8.5 times more plants, and 3.1 times more plants than 'Emerald'. In the practical sod regrowth rates observed under field conditions, where the sod cycle from harvest to harvest averages a 4 month growth cycle, the potential exists to harvest 'Diamond' three times over a 24-month time period in North Texas.

With excessive nitrogen fertilizer and its genetically controlled rhizome production, 'Diamond' may produce high levels of thatch. Close mowing (less than 12.5 mm) with a reel mower and routine verticutting will be necessary to maintain the highest quality turf with 'Diamond'.

'Diamond' was entered in the 1991 National Turfgrass Evaluation Program (NTEP) and was tested at 24 locations across the United States for over 3 years. One test was planted into a sited shaded with live oak trees on 1 Sep. 1992. Under tree shade with competition from trees for available moisture and nutrients, 'Diamond' had slightly more cover than 'Belair' and 'Meyer' (Table 8). In field sites with artifical shade, 'Diamond' was significantly improved in shade tolerance over 'Emerald' and 'El Toro' (Table 9).

When 'Diamond' was compared with 57 other zoysiagrasses for salinity tolerance, it ranked number 2 in performance, and first in reduced injury when compared to 'El Toro', 'Emerald', 'Belair', or 'Meyer' (Table 10). When compared to other commercial varieties for root growth, Diamond had less total root depth or total root mass, and produced fewer clippings than the other cultivars (Table 11).

TABLE 1

Internode length as measured between the second and third nodes, internode diameter of the third internode, and node diameter of the third node measured on zoysiagrass plants. Plants were growing in a growth chamber with a 14-hour daylength, March 1995

| Genotype | Internode length —mm— | Internode diameter —mm— | Node diameter —mm— |
|---|---|---|---|
| 'Diamond' | 15.5a | 0.79c | 0.879c |
| 'El Toro' | 39.8a | 1.45abc | 1.45abc |
| 'Meyer' | 24.1a | 1.99a | 1.99a |

*Analysis of variance by General Linear Models, with means followed by the same letter not significantly different using Tukey's Studentized Range (HSD), alpha = 0.05. Only selected means presented.

TABLE 2

Zoysiagrass internode lengths and stolon width measurements from the fourth to the fifth nodes taken February 1988 on greenhouse grown plants.

| Genotype | Internode length —mm— | Stolon width —mm— |
|---|---|---|
| 'Diamond' | 6.39e | 0.88j |
| 'Emerald' | 6.21e | 1.02ghi |
| 'Meyer' | 16.47bc | 1.53b |

*Means followed by the same letter are not significantly different using the Waller-Duncan k ratio test (k ratio = 100). Only selected means presented.

TABLE 3

Zoysiagrass leaf measurements taken February 1988 on the fourth youngest leaf from greenhouse grown plants.

| Genotype | Blade width —mm— | Blade length —mm— |
|---|---|---|
| 'Diamond' | 1.28k | 22.67f |
| 'Emerald' | 2.01fgh | 30.56ff |
| 'Meyer' | 33.3b | 82.33d |

*Means followed by the same letter are not significantly different using the Waller-Duncan k ratio test (k ratio = 100). Only selected means presented.

TABLE 4

Leaf blade width and length measured on the third youngest leaf of zoysiagrasses. Plants were growing in a growth chamber with a 14-hour daylength, March 1995.

| Genotype | Blade width —mm— | Blade length —mm— |
|---|---|---|
| 'Diamond' | 0.95d | 42.0cd |
| 'El Toro' | 3.26abc | 68.3bcd |
| 'Meyer' | 2.59c | 74.3bc |

*Analysis of variance by General Linear Models, with means followed by the same letter not significantly different using Tukey's Studentized Range (HSD), alpha = 0.05. Only selected means presented.

TABLE 5

Zoysiagrass leaf sheath length measurements taken February 1988 on the fourth youngest leaf from greenhouse grown plants.

| Genotype | Sheath length —mm— |
|---|---|
| 'Diamond' | 11.60j |
| 'Emerald' | 16.31ij |
| 'Meyer' | 30.68ed |

*Means followed by the same letter are not significantly different using the Waller-Duncan k ratio test (k ratio = 100). Only selected means presented.

TABLE 6

The number of rhizome plants indicating rhizome regrowth of experimental and commercial zoysiagrass varieties 19 and 42 days following sod harvest. Harvested at Dallas, TX in 1985.

| | DAYS PAST HARVEST | |
|---|---|---|
| VARIETY | 19 days | 42 days |
| 'Diamond' | 22.5bcd* | 93.8a |
| 'Belair' | 2.3g | 12.8e–l |
| 'Emerald' | 8.7c–g | 30.3c–h |
| 'Meyer' | 11.2f–l | |

*Means followed by the same letter are not significantly different at the P = 0.05 according to the Waller-Duncan multiple range test. Only selected means presented.

In Engelke, M. C. 1986. USGA Annual Research Report—Zoysiagrass. Table 5.

TABLE 7

Sod strength of 2-year-old stands of selected zoysiagrass varieties grown at Texas Agricultural Experiment Station—Dallas. Plots established in 1983 and harvested in 1985.

| Variety | Sod Strength Kg/cm$^2$ |
|---|---|
| 'Diamond' | 2.3 abc |
| 'Emerald' | 1.7bcdef |
| *Z. tenuifolia* | 1.8bcdef |
| 'Meyer' | 1.2cdef* |

*Means followed by the same letter in each column are not significantly different at the P = 0.05 according to Waller-Duncan Multiple Range Test. Only selected means presented.

In Engelke, M. C. 1986. USGA Annual Research Report—Zoysiagrass. Table 5.

TABLE 8

Mean turf cover, as percentage of plot during turf, during winter 1993–1994 for the 1991 NTEP zoysia trial planted under 80% shade in Dallas, TX.

| | Percentage Turf Cover | | |
|---|---|---|---|
| Variety | 10Nov93 | 21Dec93 | 22March94 |
| 'Belair' | 40.0 | 43.3 | 21.7 |
| 'Diamond' | 50.0 | 55.0 | 26.7 |
| 'Emerald' | 41.7 | 51.7 | 26.7 |
| 'El Toro' | 35.0 | 31.7 | 21.7 |
| 'Meyer' | 33.3 | 38.3 | 23.3 |
| MSD | ns | 14.5 | 10.2 |

MSD is the minimum significant difference between entry means for comparison within column, and was based on the Duncan Waller k-ratio test (k-ratio = 100). Only selected means presented.

In Morton, S. J., M. C. Engelke, and K. G. Porter. 1994. Performance of three warm-season turfgrass genera cultured in shade III. Zoysia spp. In Texas Turfgrass Research Report—1994. PR. 5242. p 27–29.

TABLE 9

Turf quality of three zoysiagrasses maintained at three shade levels, using shade cloth in field trials, in Dallas, TX.

| Variety | Full Sun | 63% Shade | 80% Shade |
|---|---|---|---|
| 'Diamond' | 8.9 | 7.2a* | 3.6a |
| 'El Toro' | 8.9 | 6.2b | 2.5b |
| 'Emerald' | 8.8 | 5.7c | 2.0b |
| MSD | ns | 0.6 | 0.6 |

MSD is the minimum significant difference between entry means for comparison within column, and was based on the Duncan Waller k-ratio test (k-ratio = 100).

S. J. Morton, T. Staton, and M. C. Engelke. 1994. Zoysiagrass shade tolerance. PR5244.

TABLE 10

Average percent shoot salt injury (average of 20 rating dates) of zoysiagrass entries.

| Variety | % Injury |
|---|---|
| 'Diamond' | 33ab |
| 'El Toro' | 38a–e |
| 'Emerald' | 42a–h |
| 'Belair' | 50f–k |
| 'Meyer' | 58lmn |

Means with the same letter are not significantly different using the Waller-Duncan k-ratio test (k-ratio = 100). Only selected means presented.

In Marcum et al. "Salt Gland Ion Secretion: A salinity tolerance mechanism among five zoysiagrass species". Submitted Crop Science 1997.

TABLE 11

Average mean root depth of zoysiagrasses grown in flexible tubes in greenhouse studies, Dallas, TX.

| Variety | Average Mean Root Depth —mm— | Total Root Weight —mg— | Clipping Weights —mg— |
|---|---|---|---|
| 'Belair' | 296 | 330 | 286 |
| 'Diamond' | 246 | 270 | 176 |
| 'El Toro' | 356 | 473 | 391 |
| 'Emerald' | 330 | 461 | 241 |
| 'Meyer' | 333 | 411 | 466 |
| MSD | 79 | 161 | 267 |

*MSD = minimum significant difference for comparison of means within columns based on the Waller-Duncan k-ratio test where k = 100. Only selected means presented.

In Marcum, K. B., M. C. Engelke, S. J. Morton, and R. H. White. 1995. Rooting characteristics and associated drought resistance of zoysiagrasses. Agron. J. 87:534–538.

EXAMPLE

DNA Fingerprint Analysis

See Caetano-Anollés, B. J. Bassam and Peter M. Gressoff, 1991, DNA Amplification fingerprinting using very short arbitrary oligonucleotide primers. Biotechnology. Vol. 9, Pp. 553–557.

The zoysiagrass amplification profiles were obtained using primer of sequence GCCCGCCC, and are compared to the standard 'Meyer' (Figure 2). Complex banding patterns and amplification fragment length polymorphisms were obtained in all cases. Results indicate bands fall into two categories, those that are common to the species, and those that in combination are characteristic of the cultivar (some identified by dots).

I claim:

1. A new and distinct variety of zoysiagrass (*Zoysia matrella* (L.) Merr.) plant as described and illustrated herein, having the principle distinguishing characteristics of white stigmas, and absence of leaf blade hairs, deep rhizomes, good recovery from sod harvest, high salinity tolerance, good shade tolerance, and a distinct DNA fingerprint.

* * * * *